(12) United States Patent
Call et al.

(10) Patent No.: US 9,370,424 B2
(45) Date of Patent: Jun. 21, 2016

(54) METHOD TO REDUCE MITRAL REGURGITATION BY CINCHING THE COMMISSURE OF THE MITRAL VALVE

(71) Applicant: Mitralign, Inc., Tewksbury, MA (US)

(72) Inventors: Aaron M. Call, Mesa, AZ (US); Joseph P. Lane, Methuen, MA (US)

(73) Assignee: MITRALIGN, INC., Tewksbury, MA (US)

( * ) Notice: Subject to any disclaimer, the term of this patent is extended or adjusted under 35 U.S.C. 154(b) by 75 days.

(21) Appl. No.: 13/770,652

(22) Filed: Feb. 19, 2013

(65) Prior Publication Data

US 2013/0190863 A1    Jul. 25, 2013

Related U.S. Application Data

(63) Continuation of application No. 12/400,350, filed on Mar. 9, 2009, now Pat. No. 8,382,829.

(60) Provisional application No. 61/035,201, filed on Mar. 10, 2008.

(51) Int. Cl.
*A61F 2/24* (2006.01)
*A61B 17/04* (2006.01)

(52) U.S. Cl.
CPC .............. *A61F 2/2442* (2013.01); *A61F 2/246* (2013.01); *A61B 17/0401* (2013.01); *A61F 2/2445* (2013.01)

(58) Field of Classification Search
CPC .............. A61B 2017/0419; A61B 2017/0487; A61B 2017/0464; A61B 2017/0496; A61B 2017/0414; A61F 2/24; A61F 2/246; A61F 2/2463; A61F 2/2478; A61F 2/2487; A61F 2/2442
See application file for complete search history.

(56) References Cited

U.S. PATENT DOCUMENTS

| | | |
|---|---|---|
| 3,841,521 A | 10/1974 | Jarvik |
| 4,339,831 A | 7/1982 | Johnson |
| 5,967,984 A | 10/1999 | Chu et al. |
| 6,050,472 A | 4/2000 | Shibata |
| 6,964,674 B1 | 11/2005 | Matsuura et al. |
| 7,037,334 B1 | 5/2006 | Hlavka et al. |
| 7,101,395 B2 | 9/2006 | Tremulis et al. |
| 7,166,127 B2 | 1/2007 | Spence et al. |
| 2002/0029080 A1 | 3/2002 | Mortier et al. |
| 2002/0128708 A1 | 9/2002 | Northrup, III et al. |
| 2002/0156526 A1 | 10/2002 | Hlavka et al. |
| 2002/0165535 A1 | 11/2002 | Lesh et al. |
| 2002/0169359 A1 | 11/2002 | McCarthy et al. |
| 2002/0173841 A1 | 11/2002 | Ortiz et al. |
| 2002/0188170 A1 | 12/2002 | Santamore et al. |
| 2003/0012034 A1 | 1/2003 | Misawa et al. |
| 2003/0018358 A1 | 1/2003 | Saadat |
| 2003/0078671 A1 | 4/2003 | Lesniak et al. |
| 2003/0120340 A1 | 6/2003 | Liska et al. |
| 2003/0199974 A1 | 10/2003 | Lee et al. |

(Continued)

*Primary Examiner* — Howie Matthews
(74) *Attorney, Agent, or Firm* — Leason Ellis LLP

(57) ABSTRACT

Methods of repairing the mitral valve and reducing mitral regurgitation. One method includes securing a first tissue anchor to a position on a posterior portion of the annular tissue of the mitral valve and a second tissue anchor to a position on an anterior portion of the annular tissue of the mitral valve. At least one tensile member spans between the first and second tissue anchors and across the orifice of the mitral valve. When tension is applied to the at least one tensile member, the posterior portion of the annular tissue is pulled toward the anterior portion.

9 Claims, 18 Drawing Sheets

(56) References Cited

U.S. PATENT DOCUMENTS

| | | |
|---|---|---|
| 2003/0208195 A1 | 11/2003 | Thompson et al. |
| 2003/0220685 A1 | 11/2003 | Hlavka et al. |
| 2003/0233142 A1 | 12/2003 | Morales et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0049211 A1 | 3/2004 | Tremulis et al. |
| 2004/0092962 A1 | 5/2004 | Thornton et al. |
| 2004/0127983 A1 | 7/2004 | Mortier et al. |
| 2004/0133063 A1 | 7/2004 | McCarthy et al. |
| 2004/0152947 A1 | 8/2004 | Schroeder et al. |
| 2004/0162568 A1 | 8/2004 | Saadat et al. |
| 2004/0162610 A1 | 8/2004 | Liska et al. |
| 2004/0167539 A1 | 8/2004 | Kuehn et al. |
| 2004/0167620 A1 | 8/2004 | Ortiz et al. |
| 2004/0172046 A1 | 9/2004 | Hlavka et al. |
| 2004/0193191 A1 | 9/2004 | Starksen et al. |
| 2004/0220473 A1 | 11/2004 | Lualdi |
| 2004/0236419 A1 | 11/2004 | Milo |
| 2004/0243153 A1 | 12/2004 | Liddicoat et al. |
| 2004/0243227 A1 | 12/2004 | Starksen et al. |
| 2004/0260317 A1 | 12/2004 | Bloom et al. |
| 2005/0049681 A1 | 3/2005 | Greenhalgh et al. |
| 2005/0055087 A1 | 3/2005 | Starksen |
| 2005/0055089 A1 | 3/2005 | Macoviak et al. |
| 2005/0065550 A1 | 3/2005 | Starksen et al. |
| 2005/0065601 A1 | 3/2005 | Lee et al. |
| 2005/0075723 A1 | 4/2005 | Schroeder et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119734 A1 | 6/2005 | Spence et al. |
| 2005/0119735 A1 | 6/2005 | Spence et al. |
| 2005/0125011 A1 | 6/2005 | Spence et al. |
| 2005/0143811 A1 | 6/2005 | Realyvasquez |
| 2005/0148815 A1 | 7/2005 | Mortier et al. |
| 2005/0149014 A1 | 7/2005 | Hauck et al. |
| 2005/0159810 A1 | 7/2005 | Filsoufi |
| 2005/0184122 A1 | 8/2005 | Hlavka et al. |
| 2005/0251157 A1 | 11/2005 | Saadat et al. |
| 2005/0251159 A1 | 11/2005 | Ewers et al. |
| 2005/0251202 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267571 A1 | 12/2005 | Spence et al. |
| 2006/0142756 A1 | 6/2006 | Davies et al. |
| 2007/0080188 A1 | 4/2007 | Spence et al. |
| 2007/0112424 A1 | 5/2007 | Spence et al. |

METHOD TO REDUCE MITRAL REGURGITATION BY CINCHING THE COMMISSURE OF THE MITRAL VALVE

This application is a continuation of U.S. patent application Ser. No. 12/400,350, filed Mar. 9, 2009, now U.S. Pat. No. 8,382,829, issued Feb. 26, 2013, which claims the priority of U.S. Provisional Patent Application Ser. No. 61/035,201, filed on Mar. 10, 2008, each of the above applications being incorporated herein by reference in its entirety.

TECHNICAL FIELD

The present invention generally relates to surgical methods of securing tissue anchors for reducing the size of an orifice through a tissue and, more particularly, methods of securing tissue anchors for reducing the circumferential orifice of the mitral valve during an annuloplasty surgical procedure.

BACKGROUND

The mitral valve is composed of valve leaflets, or flaps of tissue, that open and close tightly to ensure that the flow of blood through the heart is in one direction only. The leaflets are held in position by a ring of tissue, the annulus, surrounding and attaching the leaflets to the walls of the heart between the left atrium and left ventricle. Chordae tendineae are tendons that tether the leaflets to papillary muscles within the left ventricle, which prevent the leaflets from prolapsing into the left atrium. A dysfunction of any one of these portions of the mitral valve anatomy can cause mitral regurgitation, or the partial backflow of blood from the left ventricle into the left atrium. Depending on the severity of the condition, the individual may experience a range of symptoms, including shortness of breath, pulmonary edema, or decreased exercise tolerance.

Surgical procedures may be used for reducing mitral regurgitation. Some of these procedures have included plicating the mitral valve tissue in order to reduce the size of the orifice created between the leaflets. One such surgical procedure, annuloplasty, is particularly useful in treating mitral valve regurgitation. Annuloplasty modifies the annulus, through one or more plications, and this can return the valve to a functional geometry.

However, many annuloplasty procedures are highly invasive and may incorporate open heart surgery, which poses significant risk to the patient. Therefore, there is a need for a less invasive approach for plicating tissue by eliminating the need for open heart surgery while returning the mitral valve to a functional geometry.

SUMMARY

In one illustrative embodiment of the present invention, a method of repairing the mitral heart valve is described. The method includes securing a first tissue anchor to a position on a posterior portion of the annulus of the mitral valve and a second tissue anchor to a position on an anterior portion of the annulus of the mitral valve. At least one tensile member is spanned between the first and second tissue anchors and across the orifice of the mitral valve. When tension is applied to the at least one tensile member, the posterior portion of the annulus is pulled toward the anterior portion of the annulus.

In another illustrative embodiment of the present invention, a second method of repairing the mitral heart valve is described. This second method includes directing a guide-wire into the left ventricle, across a position on a posterior portion of the annulus, through the left atrium, across a position on the anterior portion of the annulus, and then returning into the left ventricle. A first tissue anchor is directed along the guide-wire to the position on the anterior portion of the annulus and secured. A second tissue anchor is then directed along the guide-wire to the position on the posterior portion of the annulus and secured. At least one tensile member is spanned between the first and second tissue anchors and across the orifice of the mitral valve. When tension is applied to the at least one tensile member, the posterior portion of the annulus is pulled toward the anterior portion of the annulus.

In another illustrative embodiment of the present invention, a third method of repairing the mitral heart valve is described. This third method includes directing a guide-wire into the right atrium, across the intra-atrial septum, into the left atrium to a position on the posterior portion of the annulus. A first tissue anchor is directed along the guide-wire to the position on the posterior portion of the annulus and secured. A second guide-wire is then directed into the right atrium, across the intra-atrial septum, into the left atrium to a position on the anterior portion of the annulus. A second tissue anchor is directed along the second guide-wire to the position on the anterior portion of the annulus and secured. At least one tensile member is spanned between the first and second tissue anchors and across the orifice of the mitral valve. When tension is applied to the at least one tensile member, the posterior portion of the annulus is pulled toward the anterior portion of the annulus.

DETAILED DESCRIPTION

Figure 1:
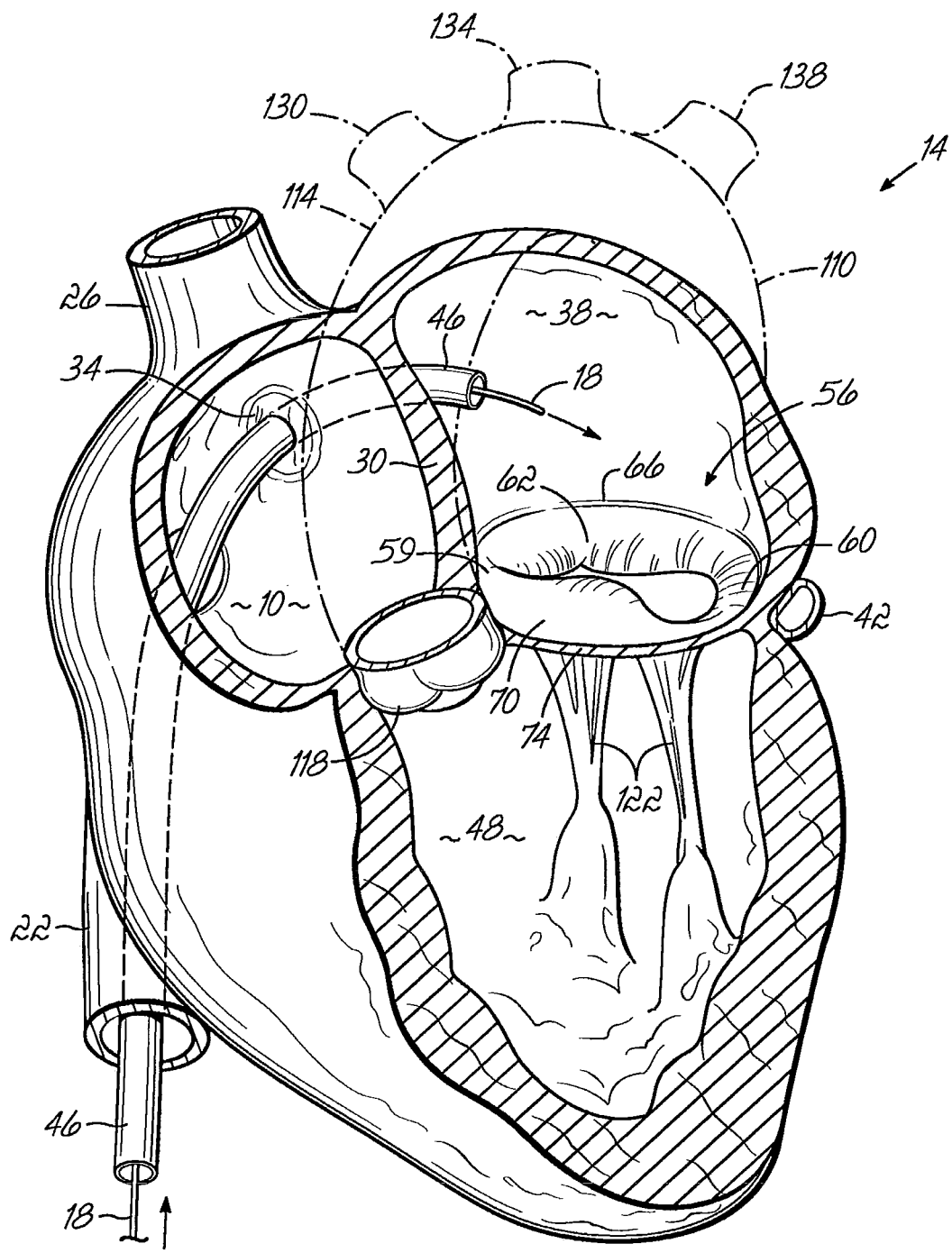
FIGS. 1-6 are respective fragmentary cross-sectional views of the heart illustrating successive steps of one exemplary procedure for advancing and securing first and second tissue anchors to the posterior and anterior annulus, respectively, of the mitral valve.

The method begins in FIG. 1 by percutaneously accessing the right atrium 10 of the heart 14 from a suitable venous access site. The venous access site can be located near the jugular vein, superiorly, from the femoral vein, inferiorly, or from other suitable superficial veins. A first guide-wire 18 is directed into the venous access site, through the inferior or superior vena cava 22, 26, as appropriate, and into the right atrium 10. Suitable guide-wires 18 can include commercially-available guide-wires commonly used in catheter-based procedures, including steerable guide-wires. The first guide-wire 18 can then be directed across the intra-atrial septum 30, for example near the fossa ovalis 34, and into the left atrium 38 in accordance with known transseptal procedures.

Though not specifically shown, the first guide-wire 18 can alternatively be directed into the left atrium 38 through other known venous access sites, such as the coronary sinus 42.

After the first guide-wire 18 is in position, a guide catheter 46 can be advanced over the first guide-wire 18 and into the left atrium 38. The guide catheter 46 can be any suitable catheter that can be directed through the vascular system to aid in the delivery of subsequent surgical devices, such as tissue anchors 50, 52 (FIG. 3 and FIG. 5) for use with the procedures described herein. Though not specifically shown, a physician can also use additional surgical instruments, such as an obturator, to sufficiently dilate the puncture through the intra-atrial septum 30 to accommodate the larger diameter guide catheter 46.

If desired, the physician can confirm the in vivo location of the guide catheter 46 during any portion of the surgical procedure by visualizing a suitable fluoroscopic marker on the distal end of the guide catheter 46 in a known manner.

Figure 2:
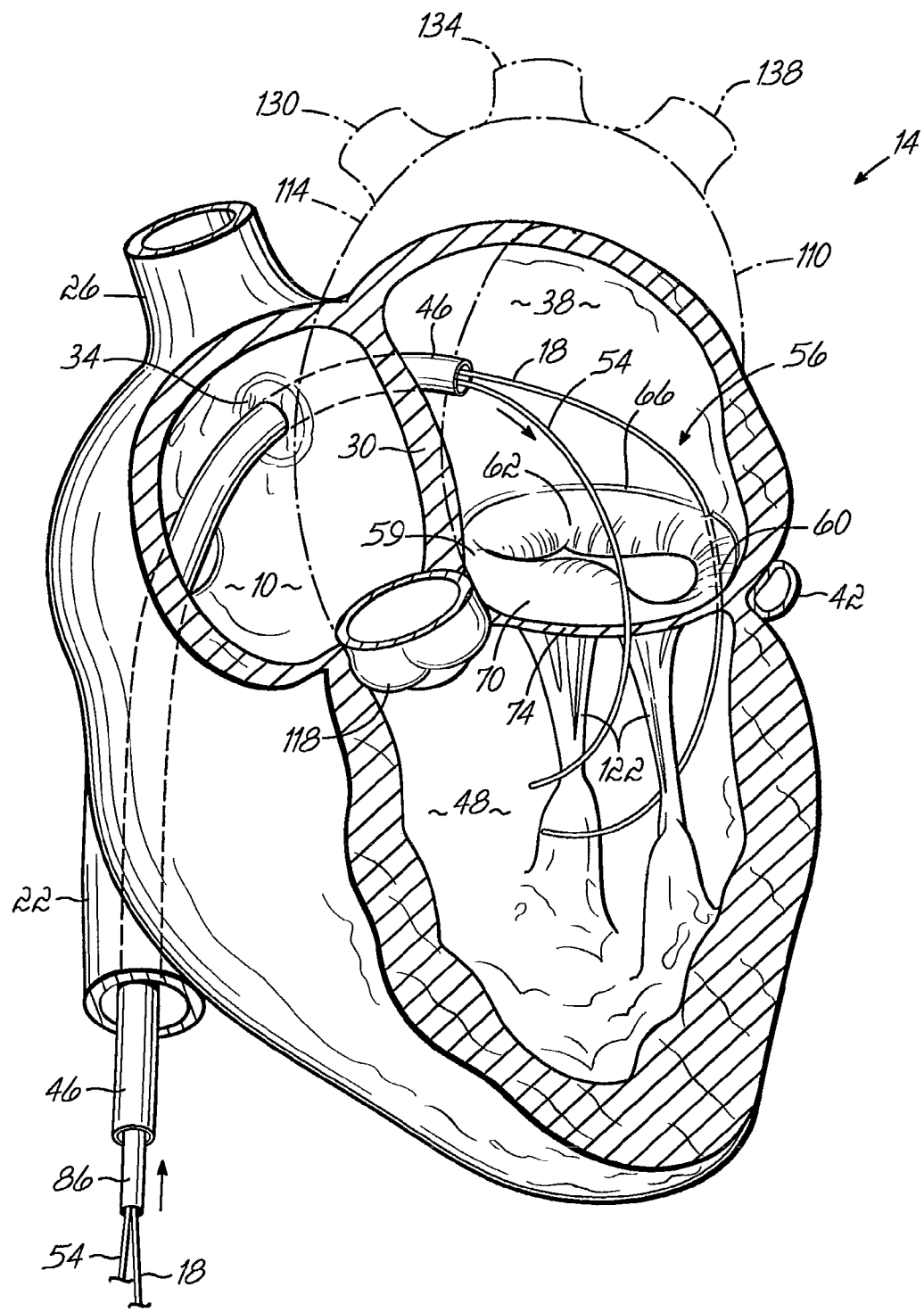

Turning now to FIG. 2 with the guide catheter 46 positioned within the left atrium 38, a second guide-wire 54 can then be directed through the lumen of the guide catheter 46 and into the left atrium 38.

FIGS. 2-8 illustrate a first embodiment of a method to repair the mitral valve 56. The first guide-wire 18 can be directed to a position on a posterior portion of the annulus (i.e. the posterior annulus 66) between the posterior and anterior commissures 59, 60. One skilled in the art may generally refer to the illustrated position as the P1 region, which is located laterally at the base of the posterior leaflet 62 along the posterior annulus 66. Another suitable position could be the P3 region, which is located medially at the base of the posterior leaflet 62 and proximal to the intra-atrial septum 30. However, the procedure should not be considered limited to these regions of the posterior annulus 66 as one or more regions may be chosen depending on the location of the enlarged orifice through the orifice of the mitral valve 56. For example, if the posterior and anterior leaflets 62, 70 do not coapt at a lateral region of the mitral valve 56, then the repair can be directed to the A1 to P1 regions; and if the posterior and anterior leaflets 62, 70 do not coapt medially, then the repair can be directed more appropriately to the A3 to P3 regions.

In the illustrated example of FIGS. 2-8, once the first guide-wire 18 is directed to the desired position on the posterior annulus 66, the first guide-wire 18 is then advanced across the posterior annulus 66 and into the left ventricle 48.

In a similar manner, the second guide-wire 54 can be directed to a position on an anterior portion of the annulus (i.e. the anterior annulus 74) between the posterior and anterior commissures 59, 60. The position of the second guide-wire 54 on the anterior annulus 74 can be spaced between the posterior and anterior commissures 59, 60 at a distance that is similar to the position and spacing of the first guide-wire 18 on the posterior annulus 66. For example, if the guide-wire 18 is positioned near the P1 region, then the second guide-wire 54 is positioned near the A1 region, which is located laterally at the base of the anterior leaflet 70 along the anterior annulus 74. Alternatively, if the first guide-wire 18 is positioned near the P3 region, then the second guide-wire 54 is positioned near the A3 region, which is located medially at the base of the anterior leaflet 70 and proximal to the intra-atrial septum 30.

Once the second guide-wire 54 is directed to the desired position on the anterior annulus 74, the second guide-wire 54 is then advanced across the anterior annulus 74 and into the left ventricle 48.

Though not shown, the physician can, if desired, use known in vivo localization techniques in directing the guide-wires 18, 54 to the desired locations along the posterior and anterior portions of the annulus 66, 74. Additionally, the guide-wires 18, 54 can include a radio-frequency (RF) energy delivery tip to assist with penetration through mitral tissue. For this purpose, a suitable RF energy device may be coupled to one or both of the guide-wires 18, 54. In yet other embodiments, the distal tip of the guide-wires 18, 54 can be pre-formed to curl back on itself to help prevent tissue damage after crossing the mitral valve tissue and entering the left ventricle 48.

Figure 3:
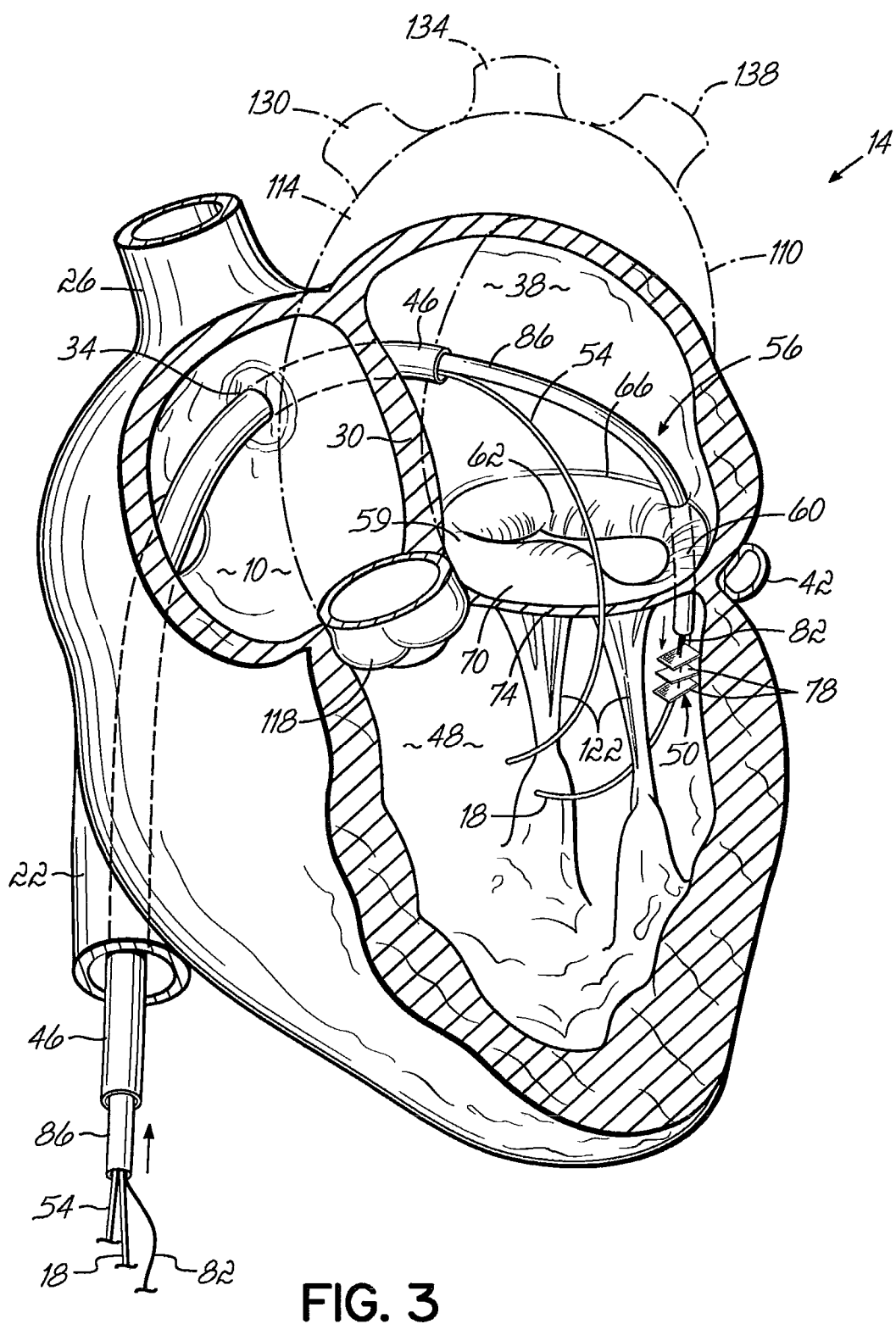

Turning now to FIG. 3, where the advancement and deployment of the first tissue anchor 50 is shown and described. While any tissue anchor device known in the art can be used, including but not limited to clips, wires, or staples, the particular tissue anchor device shown is collapsible and comprises a plurality of discrete, flat, flexible anchor elements 78 coupled by a flexible tensile member 82. The anchor elements 78 can be formed from a surgical grade fabric material (e.g., a polyester material such as DACRON) designed to promote tissue in-growth so that the anchor 50 becomes essentially encased in tissue over time. The anchor elements 78 are coupled to the tensile member 82, in this example a suture, by threading the suture upwardly through the anchor elements 78 and then back downwardly through the anchor elements 78. A slip knot is then formed, or another type of lock member is used, so that when a proximal end portion of the tensile member 82 is pulled, all of the anchor elements 78 will be drawn together against opposite sides of the annular tissue. This leaves a long "tail" of the suture leading to the venous access site for subsequent tensioning and plication, as will be described below.

In some embodiments, one or more of the anchor elements 78 can include a radiopaque marker for in vivo visualization under a suitable viewing device during the procedure. For example, one such marker can be located on a proximal portion of the tissue anchor 50 and another marker can be located on a distal portion of the tissue anchor 50.

Figure 4:
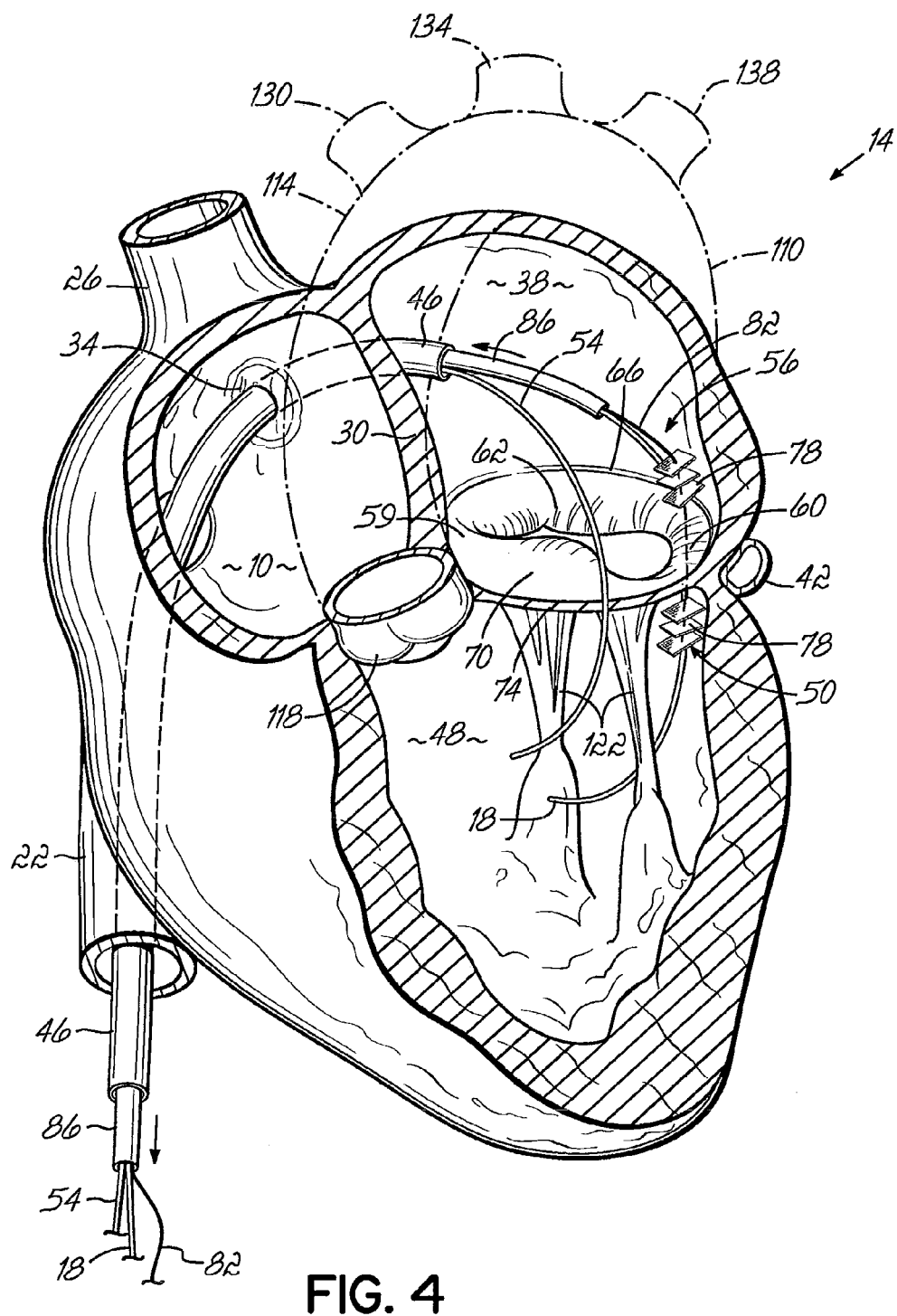

In use, the first tissue anchor 50 with a delivery sheath 86 is directed along the first guide-wire 18, across the posterior annulus 66, and into the left ventricle 48. The first tissue anchor 50 is then at least partially deployed from the delivery sheath 86 on the left ventricular side of the posterior annulus 66. As necessary, the first guide-wire 18 can be removed before or after the tissue anchor deployment process. Once a sufficient portion of the first tissue anchor 50 has been deployed within the left ventricle 48, the physician can stop deploying the anchor elements 78, slightly retract the delivery sheath 86 back across the posterior annulus 66 into the left atrium 38, and then deploy the remainder of the anchor elements 78 of the tissue anchor 50 within the left atrium 38, as shown in FIG. 4.

Figure 5:
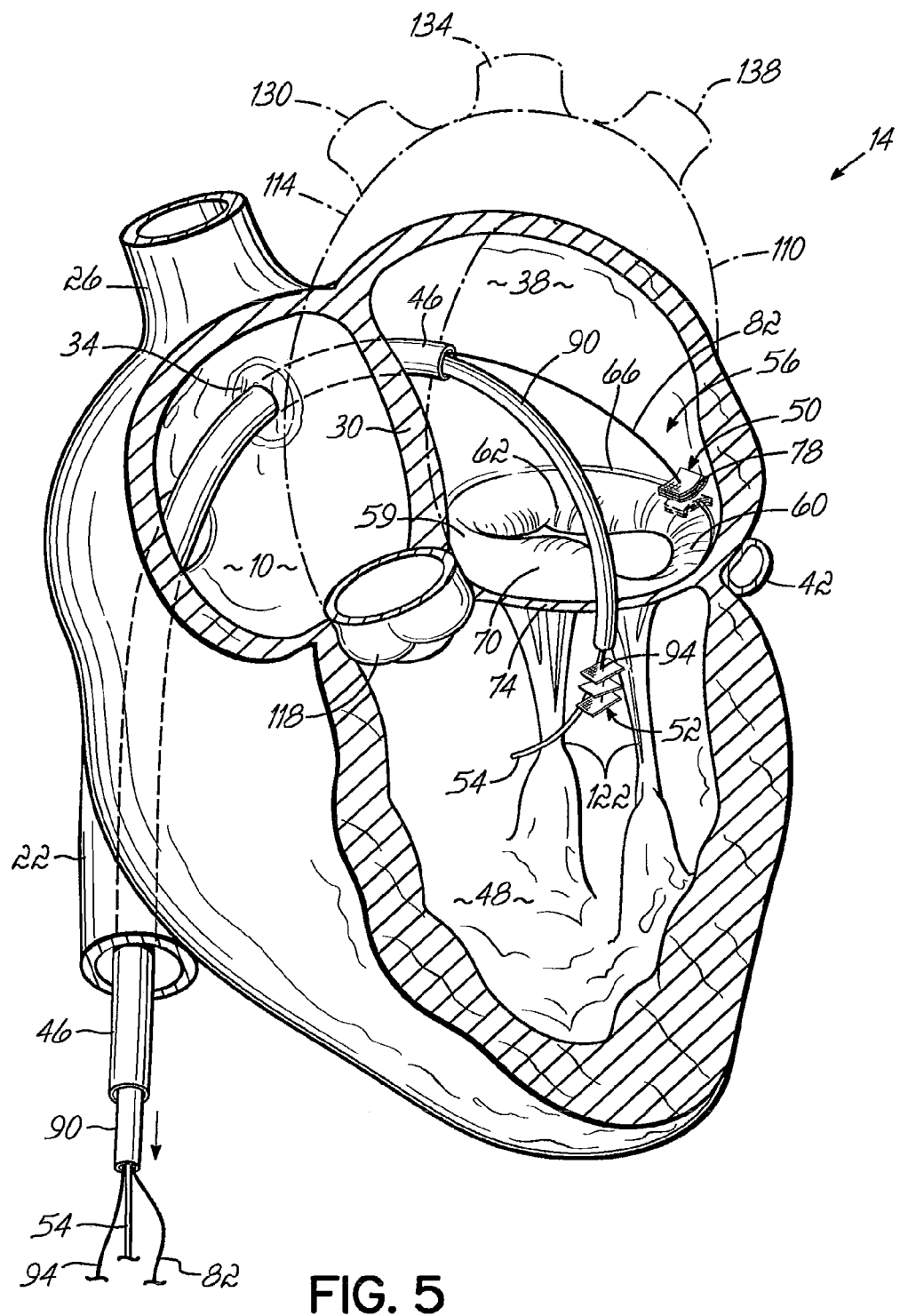

In FIG. 5, the physician pulls on the proximal end portion of the tensile member 82 such that the anchor elements 78 of the first tissue anchor 50 are drawn together against opposite sides of the annular tissue, thereby securing the first tissue anchor 50 to the P1 region of the posterior annulus 66.

Also shown in FIG. 5, once the first tissue anchor 50 is secured, the physician can then begin directing the second tissue anchor 52, with a delivery sheath 90, along the second guide-wire 54, across the anterior annulus 74, and into the left ventricle 48. As described above, the second tissue anchor 52 is then at least partially deployed from the delivery sheath 90 within the left ventricle 48, the delivery sheath 90 is then retracted back across the anterior annulus 74, and the remainder of the second tissue anchor 52 is deployed within the left atrium 38.

While the second tissue anchor 52 has been shown to be similar to the first tissue anchor 50, it would be understood that a different tissue anchor device structure, or manner of deployment, could be used.

Figure 6:
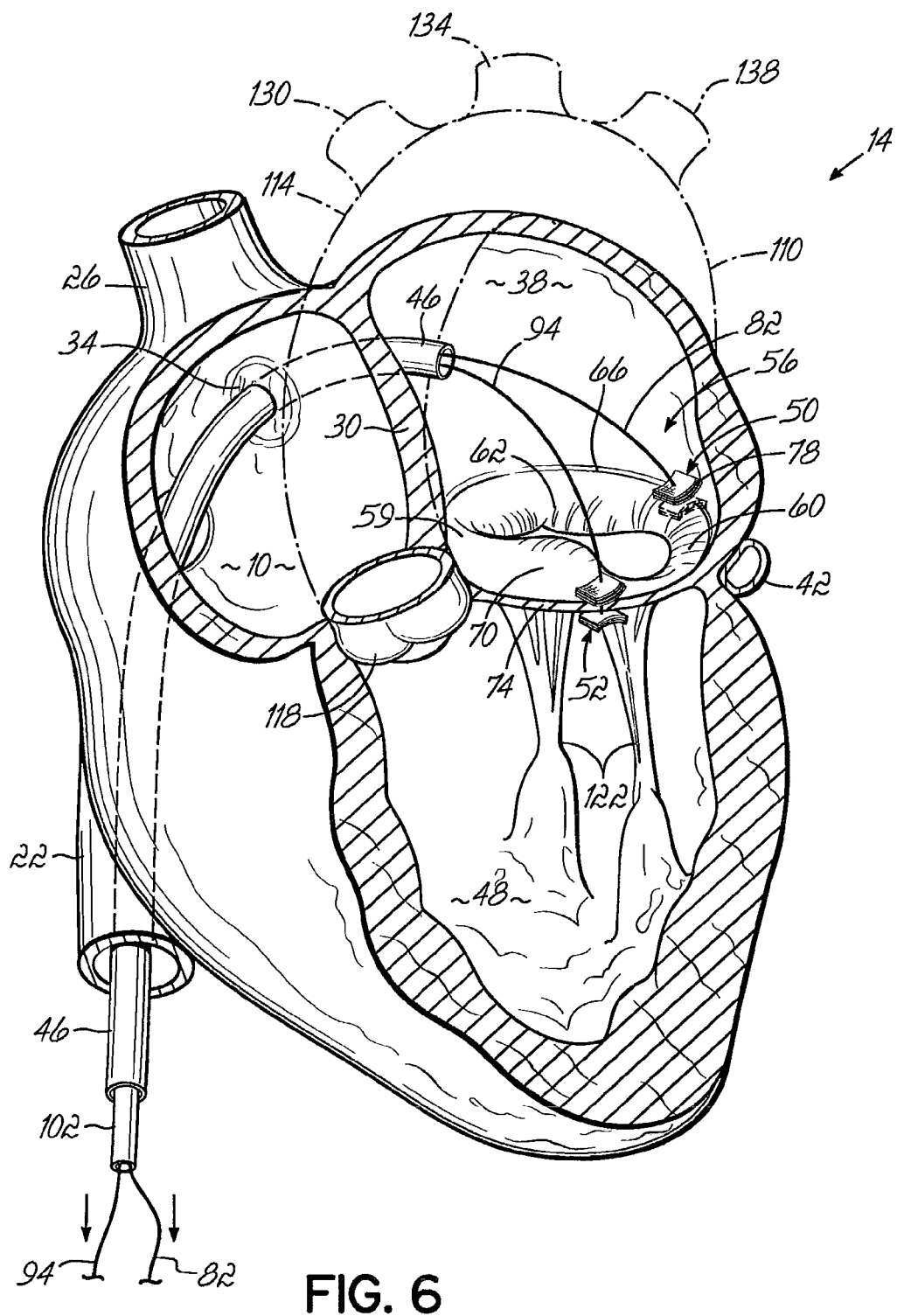

In FIG. 6, after the second tissue anchor 52 has been deployed and secured to the anterior annulus 74 by a tensile member 94, the physician can then retract the delivery sheath 90 from the surgical site.

Figure 7:
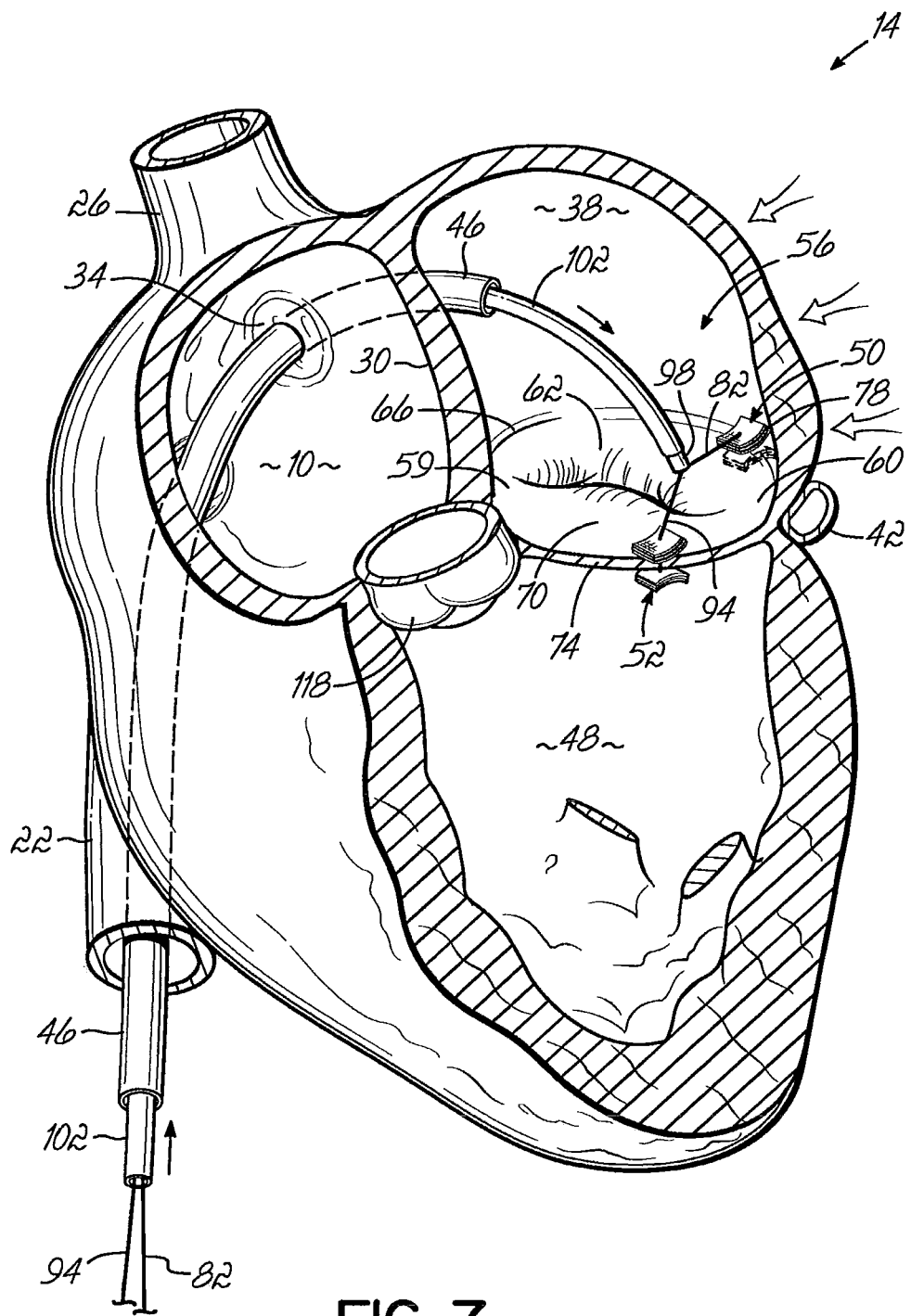
FIGS. 7-8 are respective fragmentary cross-sectional views of the heart illustrating successive steps of one exemplary procedure for reducing the size of the mitral valve orifice by tensioning the tensile members extending between the first and second tissue anchors.

With both the first and second tissue anchors 50, 52 secured to their respective positions on the posterior and anterior portions of the annulus 66, 74, respectively, the physician can then plicate the tissue, as shown in FIG. 7. To plicate the tissue, the physician can pull on the respective proximal end portions of the tensile members 82, 94 such that the posterior annulus 66 is pulled toward the anterior annulus 74. The plication and position of the tissue can be maintained by directing a suture locker 98 along the tensile members 82, 94 to the surgical site. The advancing of the suture locker 98 can be accomplished with a delivery catheter 102 in accordance with known methods. Suitable suture lockers 98 can include those shown in U.S. application Ser. No. 11/425,731, which allows the physician to lock the tension and simultaneously cut the tensile members 82, 94 to an appropriate length, or the suture locker 98 described in U.S. application Ser. No. 11/753,921, which includes a locker body having a passageway through which the tensile members 82, 94 extend and a slidable member that moves from a latent condition to an activated condition to lock the position of the tensile members 82, 94 relative to the locker 98.

Figure 8:
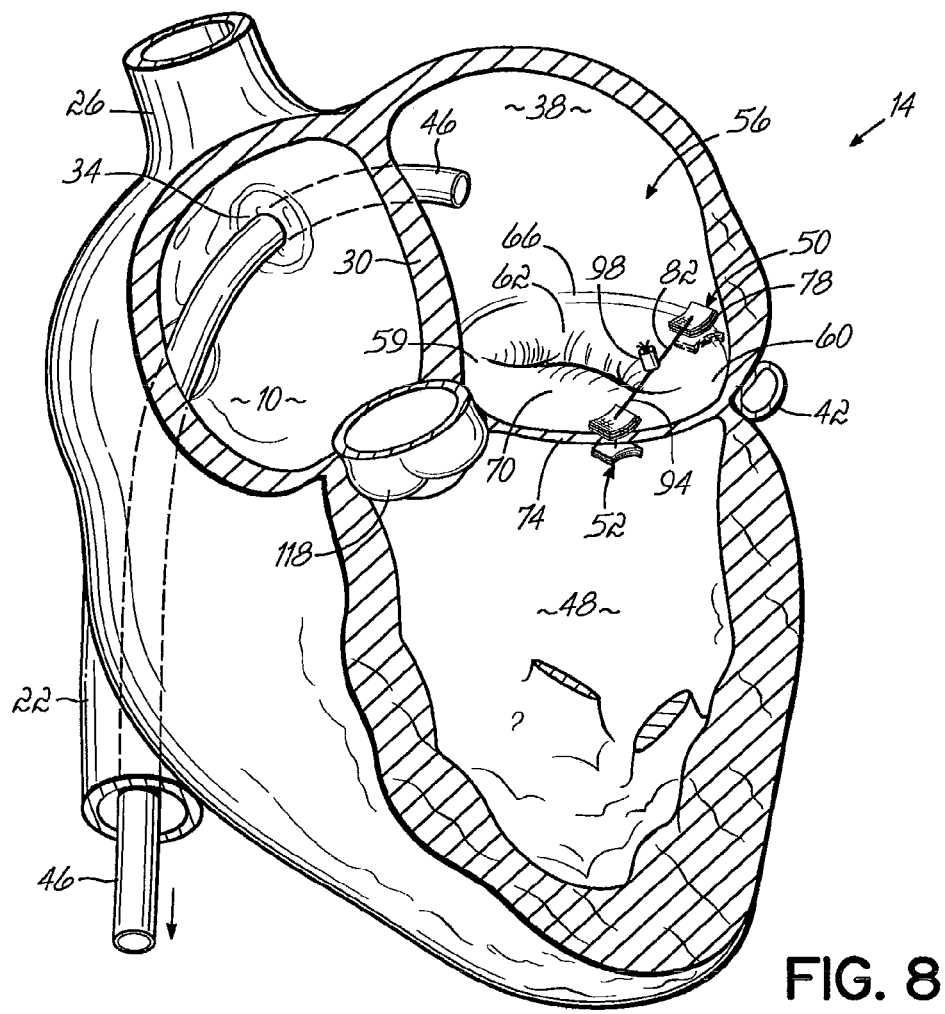
Figure 9:
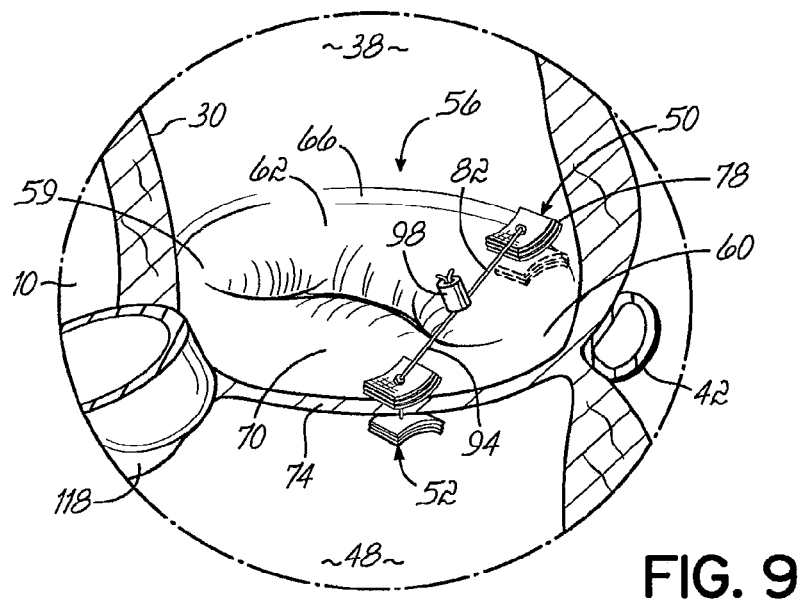
FIG. 9 is an enlarged cross-sectional view of the repaired mitral valve resulting from the procedures illustrated in FIGS. 1-8.

FIG. 8 illustrates the surgical site after the suture locker 98 is in position, the tensile members 82, 94 are locked relative to the suture locker 98, the tensile members 82, 94 have been cut, and the delivery catheter 102 retracted. This is also illustrated, with an enlarged view, in FIG. 9. As shown, the first and second tissue anchors 50, 52 are secured and tensioned with the locker 98 such that the posterior and anterior leaflets 62, 70 come into contact and mitral regurgitation is reduced.

Though not specifically shown, the physician can then direct an atrial septal defect closure device to the intra-atrial septum 30 to seal the orifice created by the guide catheter 46 after it has been retracted from the surgical site. Atrial septal defect closure devices are known generally, and can include commercially-available examples such as the BIOSTAR by NMT Medical, Inc. or the AMPLATZER Septal Occluder by AGA Medical Corp.

With the first method of repairing the mitral valve 56 described with some detail, a second exemplary surgical procedure for repairing the mitral valve 56 can now be described with reference to FIGS. 10-13. In this method of repairing the mitral valve 56, the physician approaches the mitral valve 56 from within the left ventricle 48.

Figure 10:
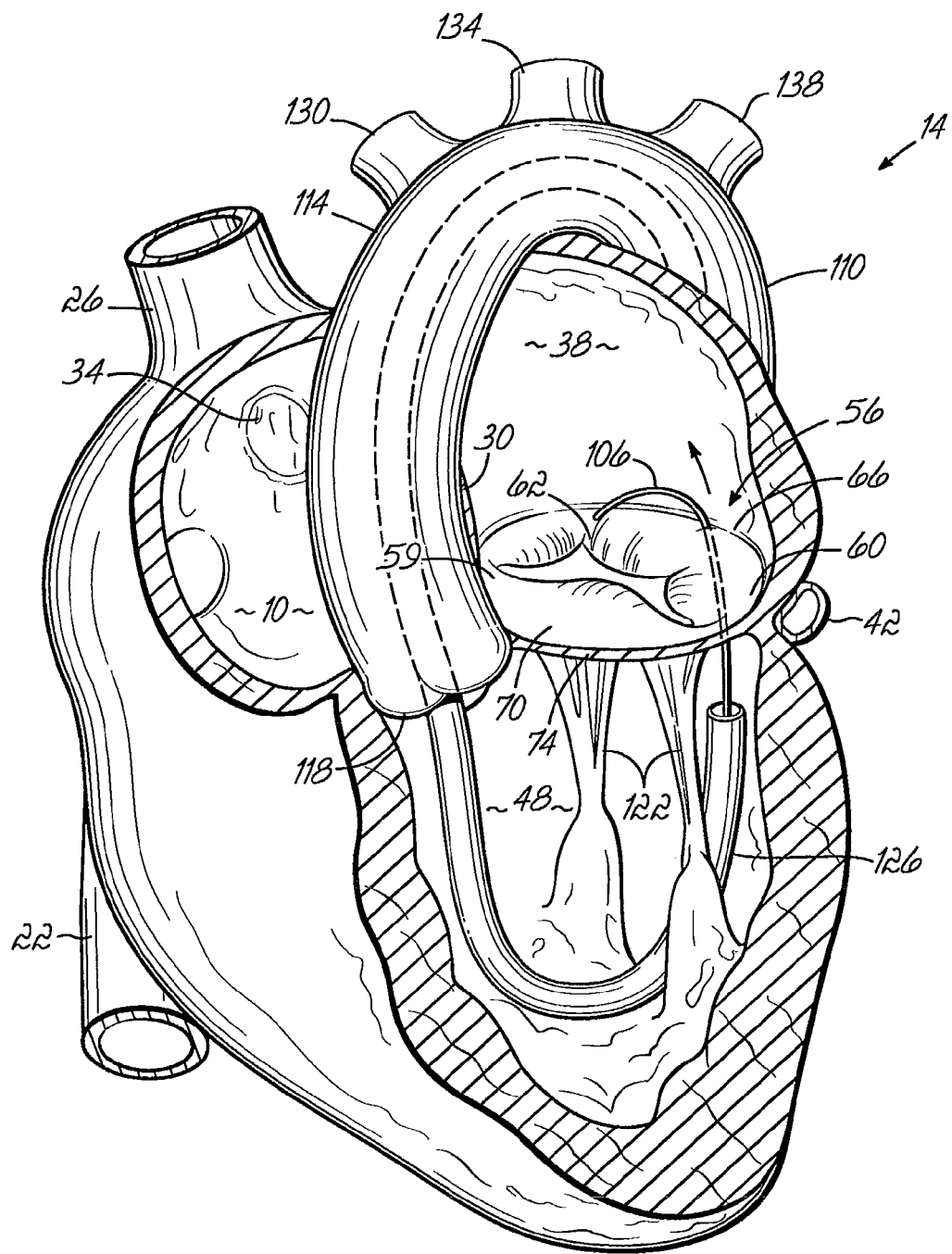
FIGS. 10-13 are respective fragmentary cross-sectional views of the heart illustrating successive steps of another exemplary procedure for advancing and securing first and second tissue anchors to the posterior and anterior portions of the annulus, respectively, of the mitral valve.

FIG. 10 illustrates the directing of a guide-wire 106 into the left ventricle 48, across the mitral valve 56, and into the left atrium 38. This can be accomplished in a known way, such as directing the guide-wire 106 from a suitable arterial access site located near the femoral or iliac arteries. The guide-wire 106 is directed from the arterial access site to the aorta 110, around the aortic arch 114, through the aortic valve 118, and between the pair of chordae tendineae 122 in the left ventricle 48. As described previously, the guide-wire 106 is then followed by a guide catheter 126.

Though not specifically shown, the percutaneous access can alternately be made from a superior arterial access site so that the guide-wire 106 is directed into the aortic arch 114 from the brachiocephalic trunk 130, the left common carotid 134, or the left subclavian arteries 138.

Once the guide-wire 106 is within the left ventricle 48, it can be steered through the volume of the left ventricle 48 to the mitral valve 56. More specifically, the guide-wire 106 is steered to cross the mitral valve 56 at the posterior annulus 66. While the mitral valve 56 can be crossed at several locations, it is preferred that the guide-wire 106 crosses the posterior annulus 66 between the anterior and posterior commissures 74, 66 at approximately the P1 region, as shown in FIG. 10. While this embodiment of the present invention has been illustrated with the guide-wire 106 crossing the P1 region, it would be understood that other regions of the posterior annulus 66, i.e. the P2 or P3 regions, could also be used if appropriate. The P1 region can be localized in vivo through fluoroscopy while the physician advances the guide-wire 106 across the P1 region and into the left atrium 38. As noted above, if desired, the guide-wire 106 can have a radio-frequency (RF) energy delivery tip for assisting with penetration through mitral tissue.

After the guide-wire 106 enters the left atrium 38, it is steered through the volume of the left atrium 38 to the A1 region of the anterior annulus 74. The guide-wire 106 then crosses the anterior annulus 74 at the A1 region and reenters the left ventricle 48.

Figure 11:
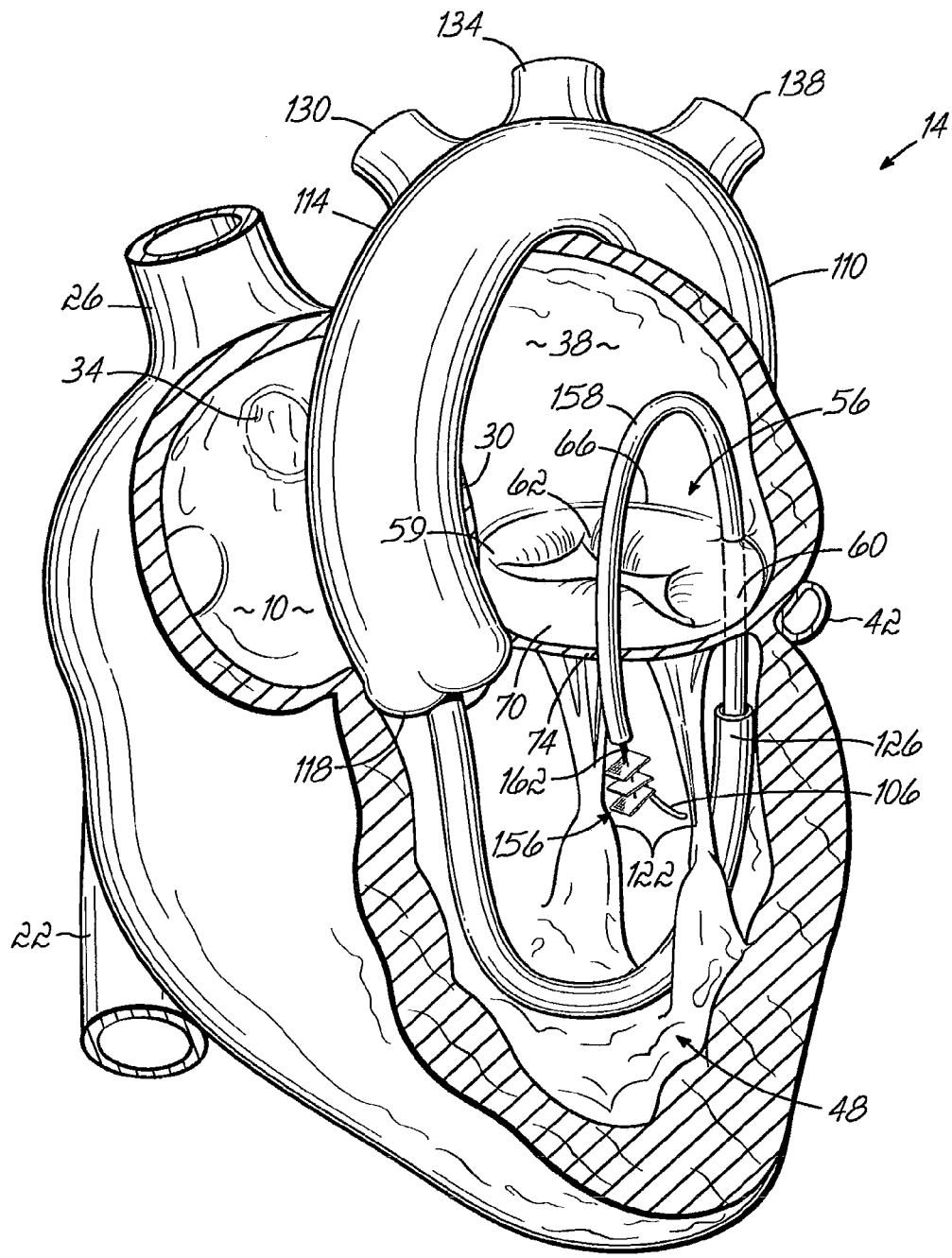

As shown in FIG. 11, with the guide-wire 106 properly positioned, the surgeon can direct a first tissue anchor 156 with the delivery catheter 158 through the guide catheter 126, along the guide-wire 106, across the A1 region, and into the left ventricle 48. While any suitable tissue anchor device can be used, the tissue anchor 156 illustrated is the same as those described above. Accordingly, the first tissue anchor 156 is at least partially deployed from the delivery catheter 158 on the left ventricular side of the anterior annulus 74. As necessary, the guide-wire 106 can be removed before or after the tissue anchor deployment process. Once a sufficient portion of the first tissue anchor 156 has been deployed within the left ventricle 48, the physician can stop deploying, retract the delivery catheter 158 back across the anterior annulus 74 into the left atrium 38, and then deploy the remainder of the first tissue anchor 156 within the left atrium 38, as shown in FIG. 12.

Figure 12:
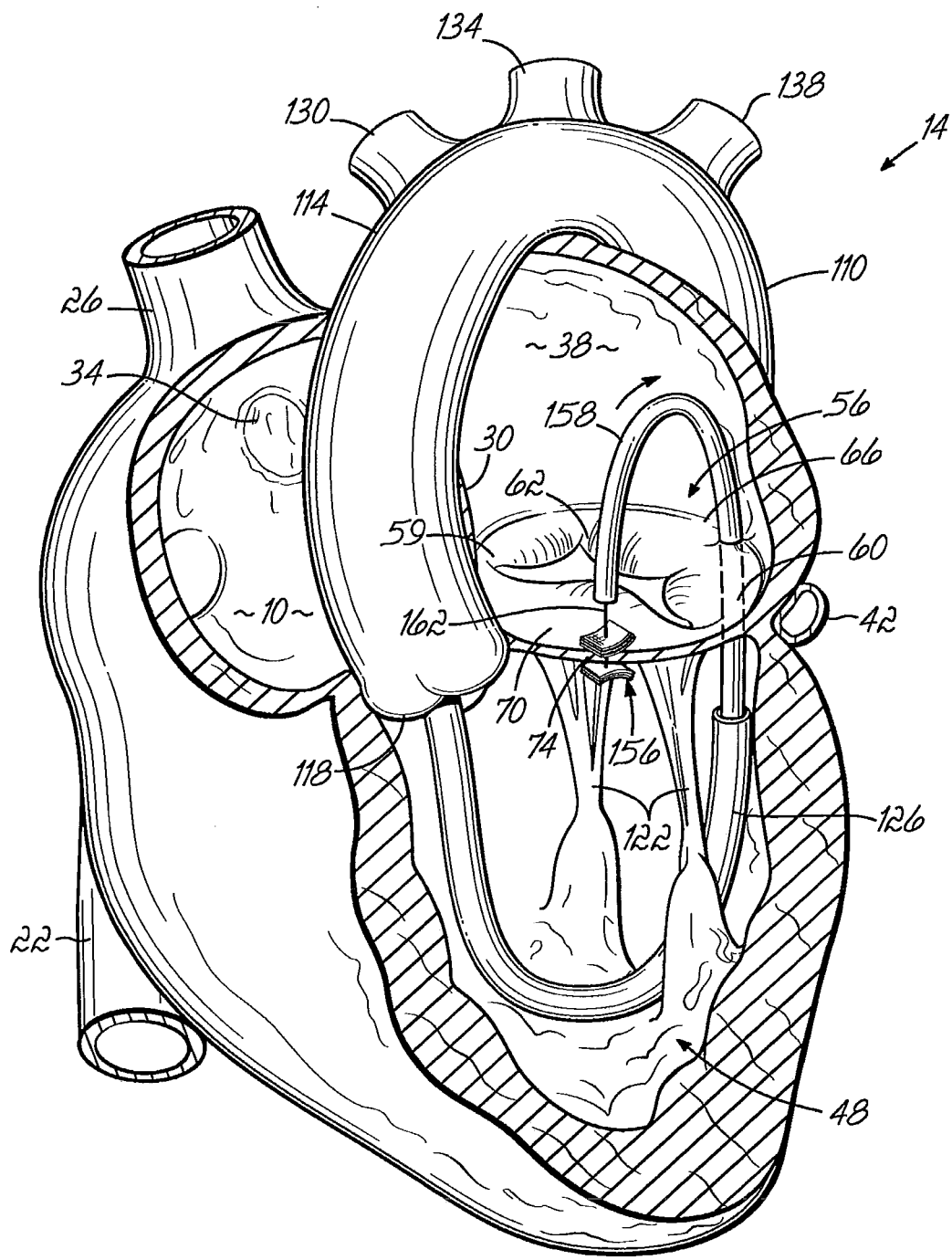

FIG. 12 also illustrates that the physician can then pull on the proximal end portion of the tensile member 162 of the first tissue anchor 156 such that the first tissue anchor 156 is secured to the A1 region of the anterior annulus 74.

Figure 13:
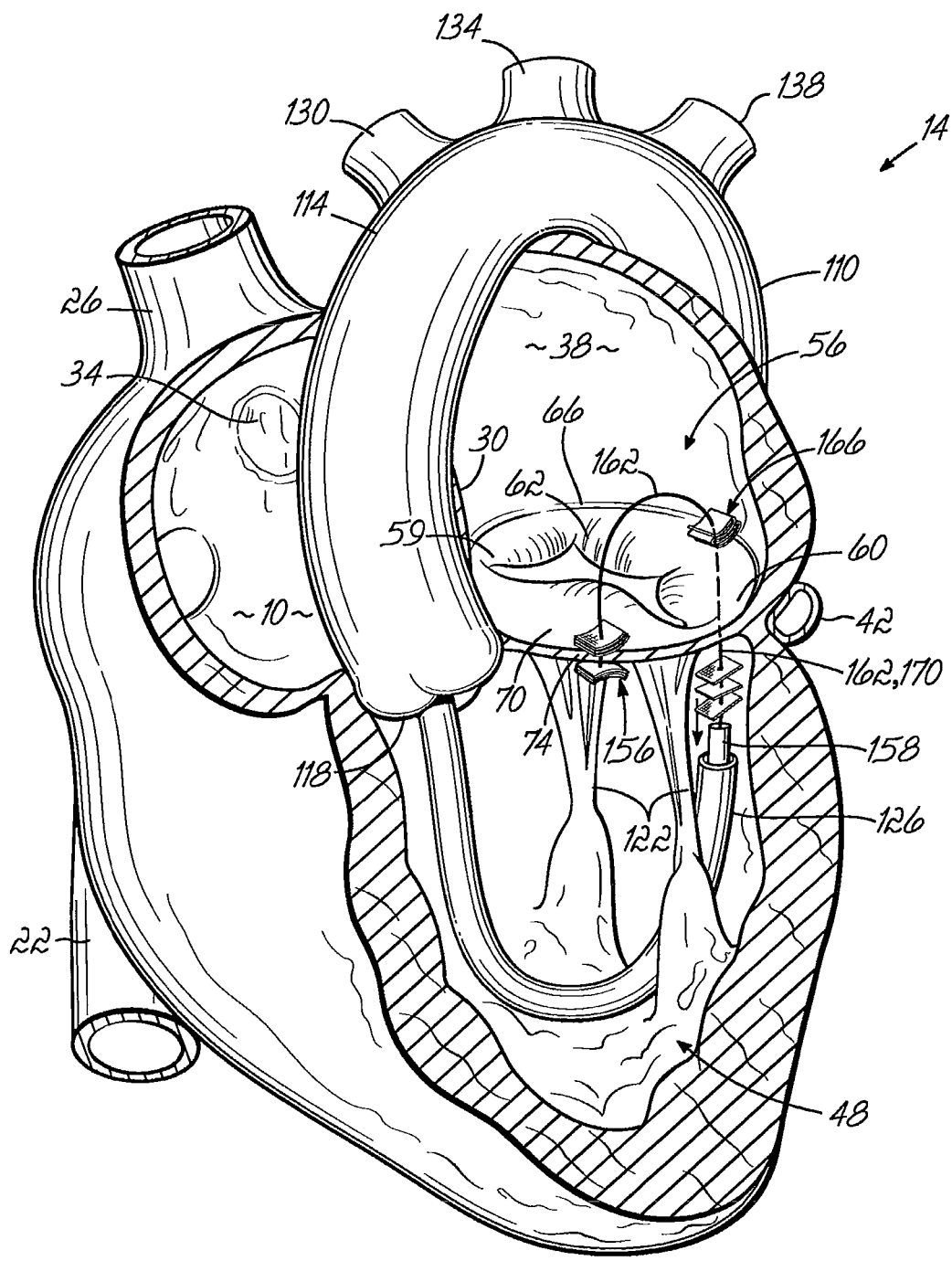

FIG. 13 illustrates the directing and deploying of a second tissue anchor 166 along the tensile member 162 at the P1 region of the posterior annulus 66. As shown, the second tissue anchor 166 has a structure that is similar to the first tissue anchor 156; however, this is not required. Thus, deployment of the second tissue anchor 166 can occur in a manner similar to the procedures described above.

Figure 14:
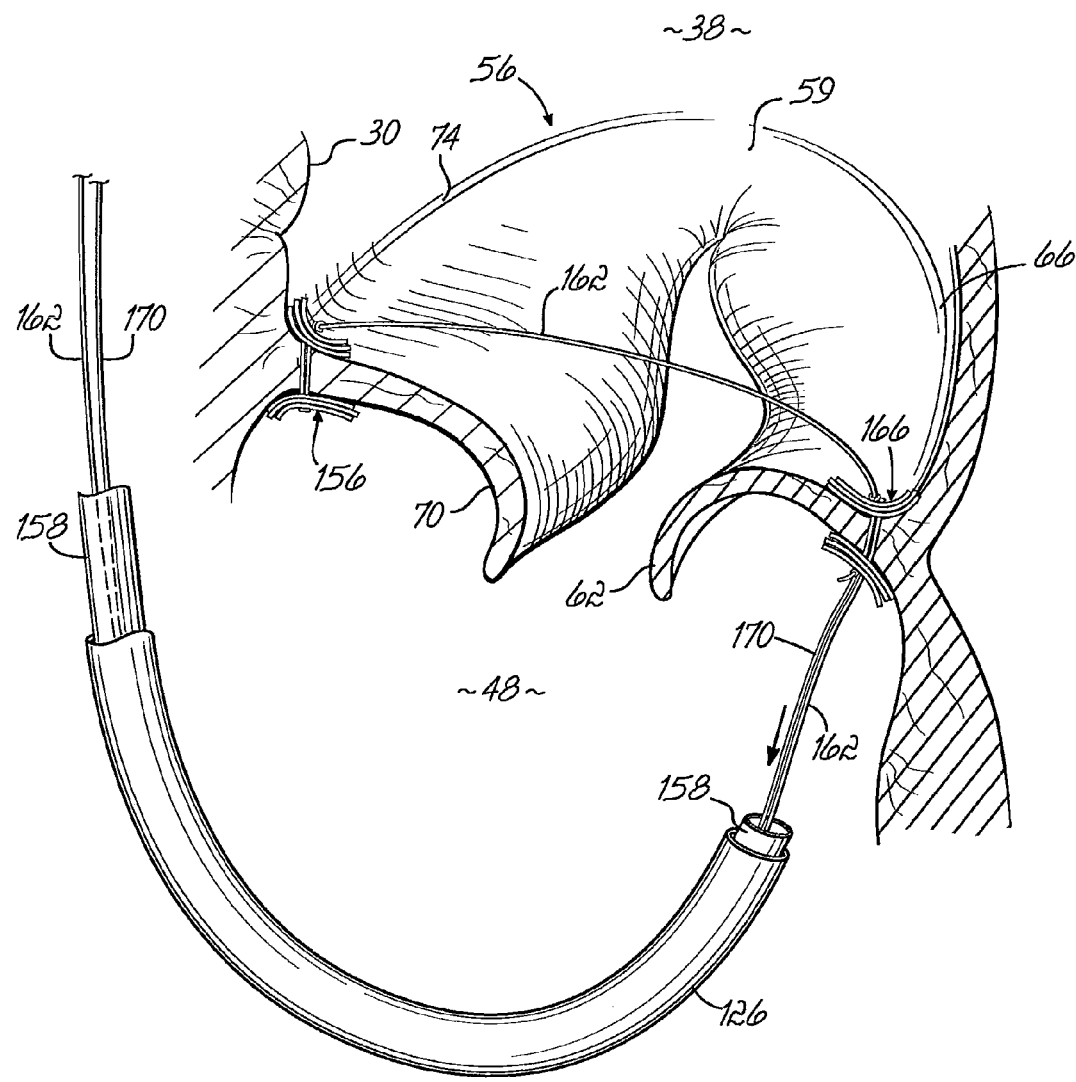
FIG. 14 is an enlarged cross-sectional view of the heart illustrating the first and second tissue anchors secured to the posterior and anterior annulus, resulting from the procedure illustrated in FIGS. 10-13.

FIG. 14 is an enlarged view of the mitral valve 56 with the first and second tissue anchors 156, 166 positioned and secured to the anterior and posterior portions of the annulus 74, 66, respectively. The tensile members 162, 170 of the first and second tissue anchors 156, 166, respectively, extend proximally from the surgical site, through the guide catheter 126 to the incision site.

Figure 15:
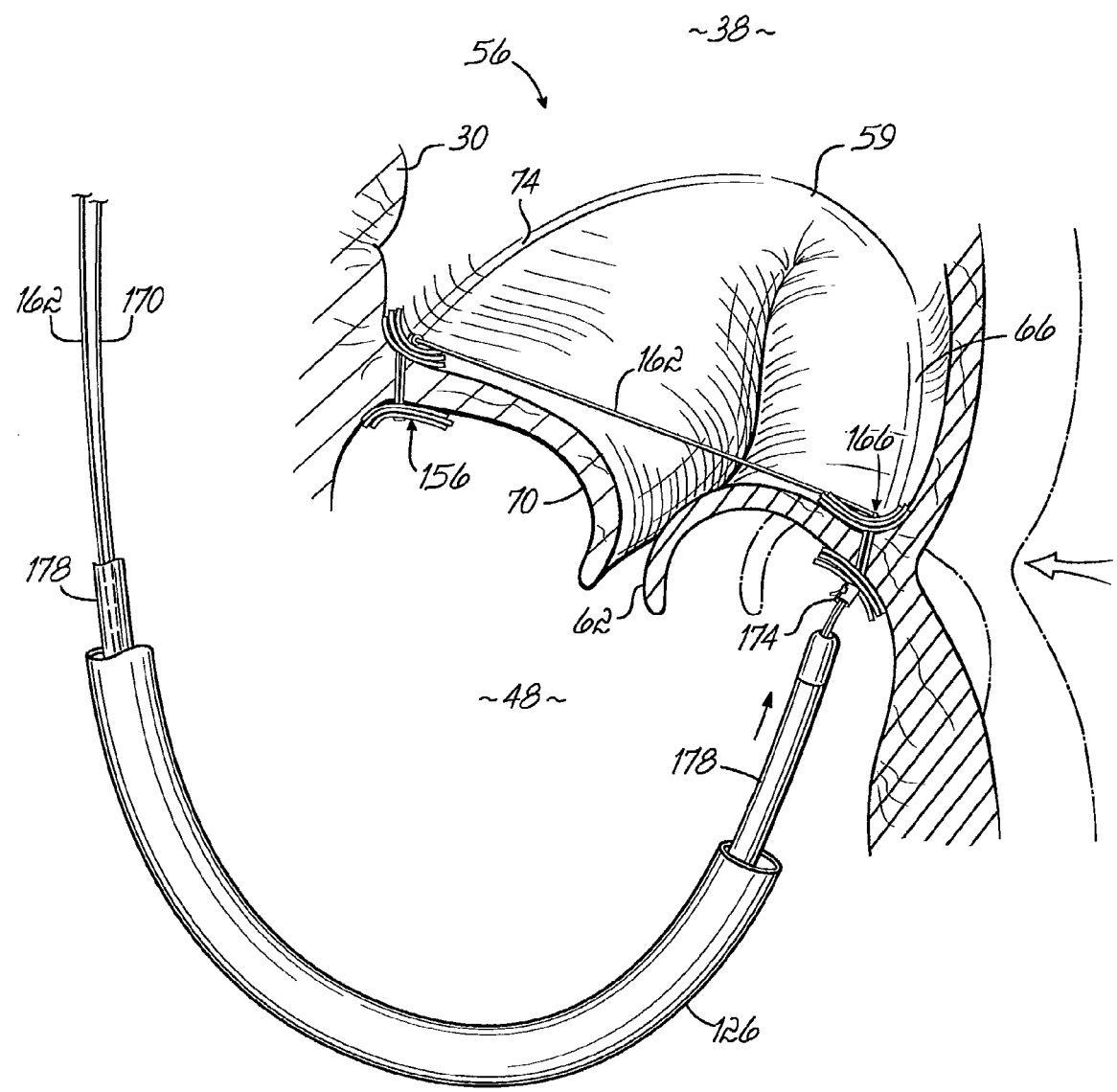
FIG. 15 is an enlarged cross-sectional view illustrating an exemplary method of reducing the size of the mitral valve orifice by tensioning a tensile member extending between the first and second tissue anchors.
Figure 16:
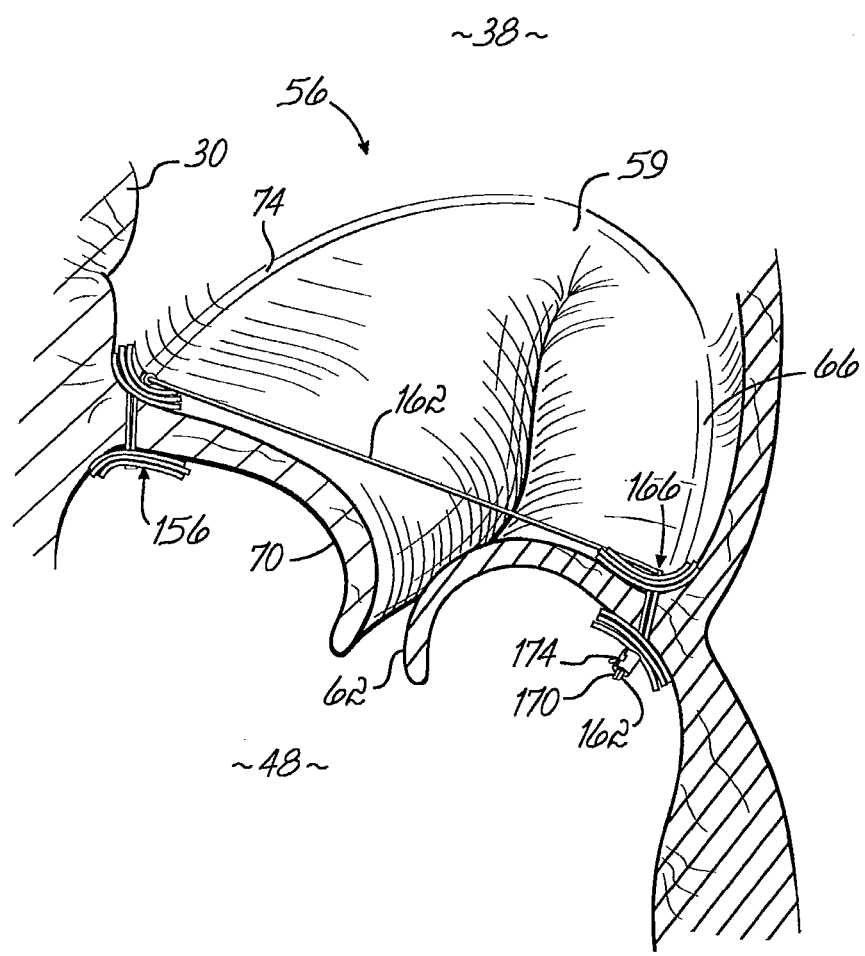
FIG. 16 is an enlarged cross-sectional view of the repaired mitral valve resulting from the procedure shown in FIGS. 10-15.

In FIG. 15, the physician pulls proximally on the tensile members 162, 170, such that the A1 and P1 regions are pulled together, the anterior and posterior leaflets 70, 62 coapt, and mitral regurgitation is reduced. FIG. 15 further illustrates the advancing of a suitable locker 174 with a delivery catheter 178 to the surgical site such that the reduction in the size of the mitral valve 56 is maintained. The locker 174 can be any suitable suture locker device, including those described previously. The tensile members 162, 170 are then cut to an appropriate length and the surgical device retracted from the surgical site. The result of the surgical procedure, illustrated in FIG. 16, is the first and second tissue anchors 156, 166 are secured to the annular tissue, and the tensile member 162, 170 extending from the first and second tissue anchors 156, 166 are sufficiently tensioned such that the anterior and posterior leaflets 70, 62 coapt and mitral regurgitation is reduced or eliminated.

Figure 17A:
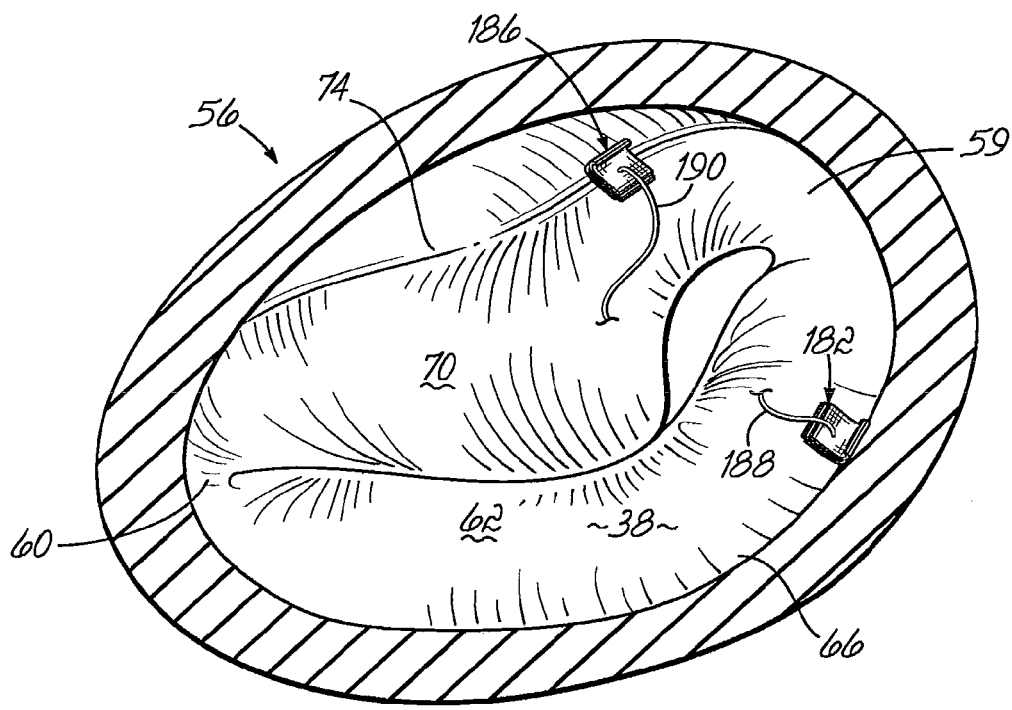
FIG. 17A is a top view illustrating the mitral valve from the left atrium before tissue plication and with the first and second tissue anchors positioned at the P3 and A3 regions, respectively.
Figure 17B:
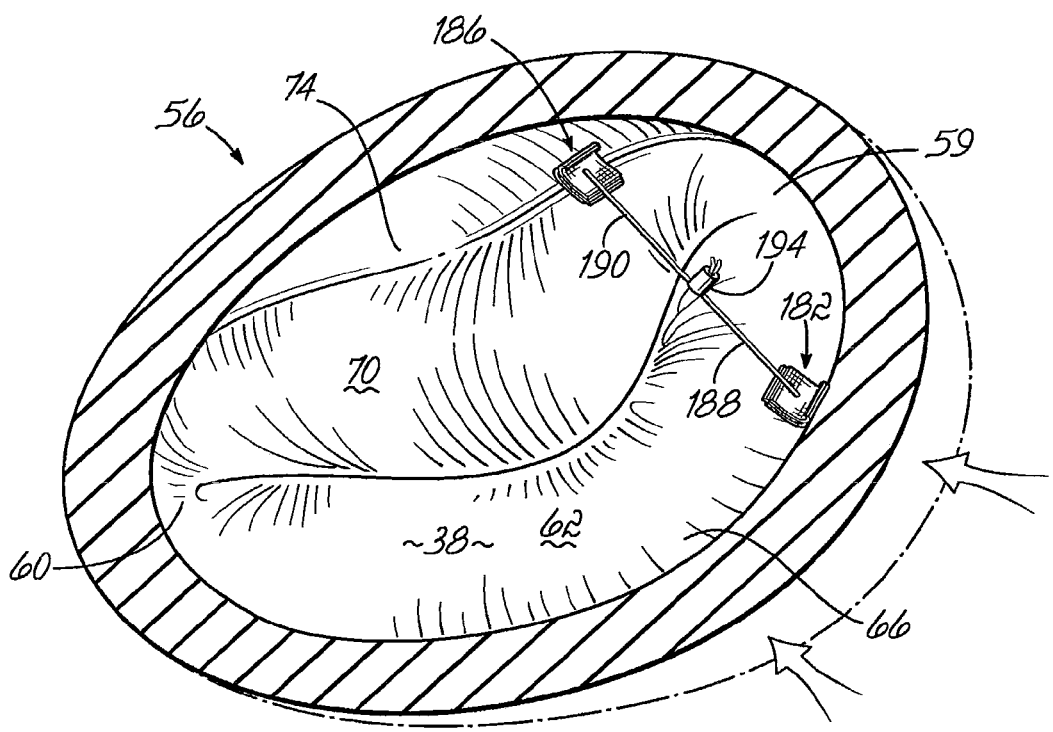
FIG. 17B is a top view illustrating the mitral valve from the left atrium after tissue plication and with the first and second tissue anchors positioned at the P3 and A3 regions, respectively.

While the methods of mitral valve repair have been described and illustrated primarily with the tissue anchor devices being located at the A1 and P1 regions of the annular tissue, it would be understood that other regions of annular tissue could also be used. For example, FIG. 17A illustrates the mitral valve 56 from within the left atrium 38 having tissue anchors 182, 186 positioned substantially near the P3 region of the posterior annulus 66 and A3 region of the anterior annulus 74, respectively, and prior to repair of the mitral valve 56. Accordingly, tensile members 188, 190 extend from the tissue anchors 182, 186, but are not yet tensioned. FIG. 17B illustrates the tensioning and locking of the tensile members 188, 190 with a suitable locker 194, such as those described previously. Accordingly, the posterior annulus 66 is pulled toward the anterior annulus 74 and mitral regurgitation is reduced.

Figure 17C:
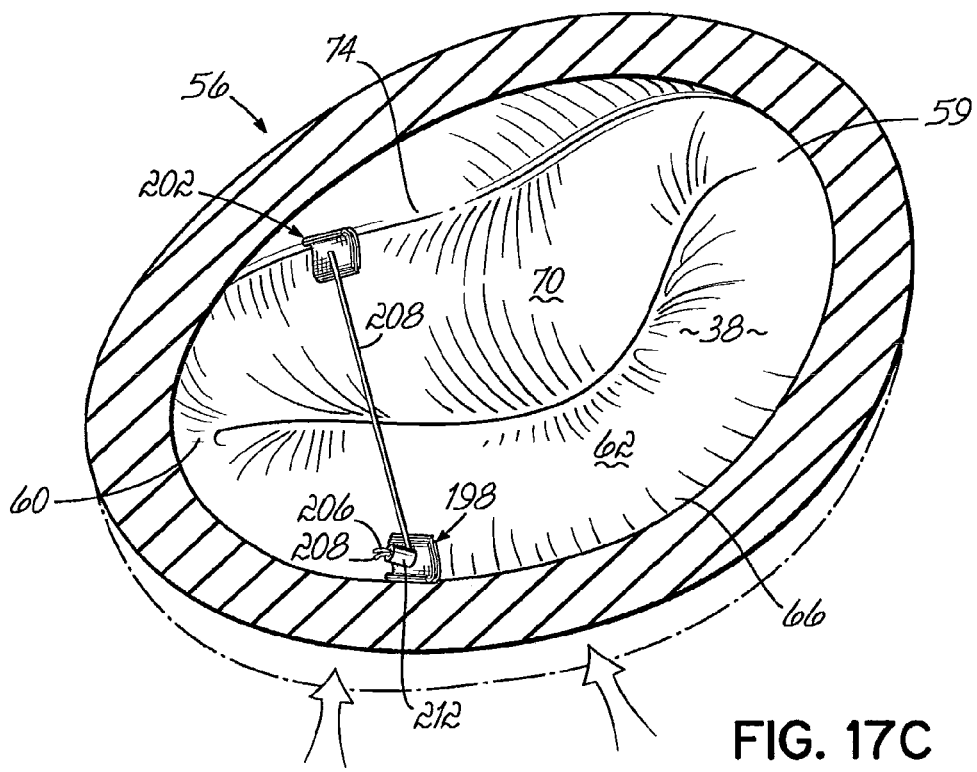
FIG. 17C is a top view illustrating the mitral valve from the left atrium after tissue plication and with the first and second tissue anchors positioned at the P1 and A1 regions, respectively.

FIG. 17C illustrates tissue anchors 198, 202 positioned substantially near the P1 region of the posterior annulus 66 and A1 region of the anterior annulus 74, respectively, as described in the methods above. Tensile members 206, 208 are tensioned and locked with a suitable locker 212 such that the posterior annulus 66 is pulled toward the anterior annulus 74 and mitral regurgitation is reduced.

As discussed above, the positions of the tissue anchor devices would be primarily determined by the location of the largest orifice through the mitral valve 56. That is, if the posterior and anterior leaflets 62, 70 do not coapt near the posterior commissure 59, then tissue anchors 182, 186 positioned at the A3 and P3 regions can provide the most beneficial repair; if the posterior and anterior leaflets 62, 70 do not coapt near the anterior commissure 60, then tissue anchors 198, 202 positioned at the A1 and P1 regions can provide the most beneficial repair. However, if the posterior and anterior leaflets 62, 70 do not coapt at a position that is between the posterior and anterior commissures 59, 60, or if there is more than one region at which the leaflets 62, 70 do not coapt, then one or more regions can be chosen to include additional tissue anchors to effectuate a mitral valve repair.

Figure 17D:
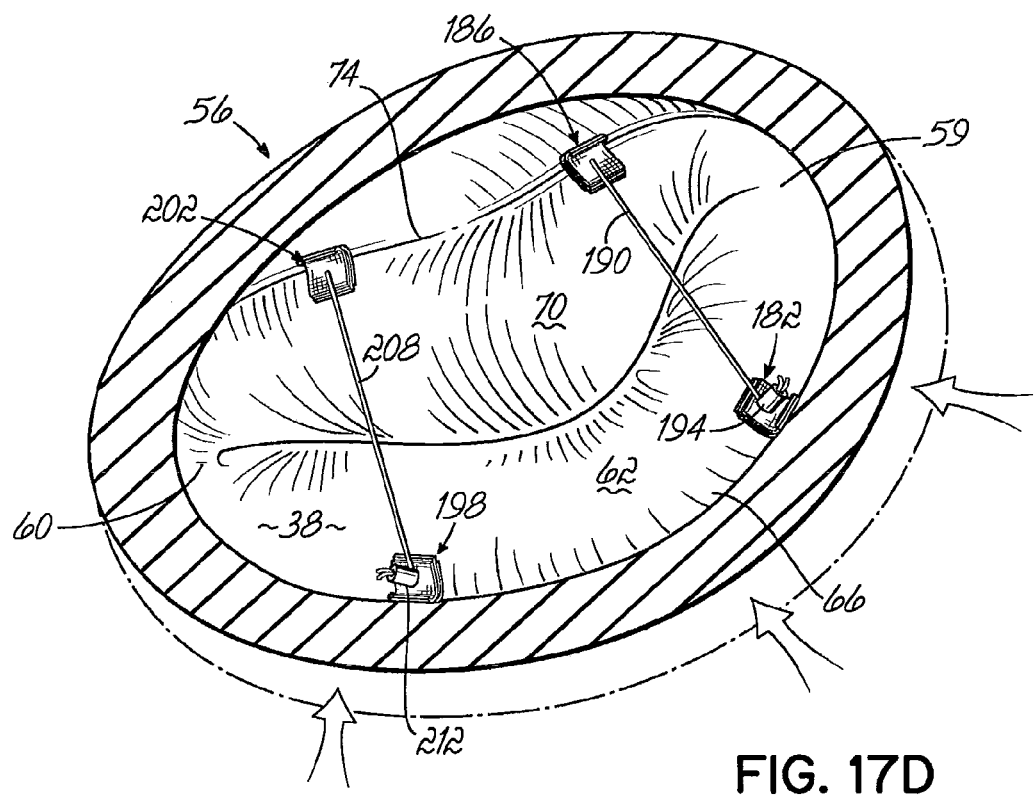
FIG. 17D is a top view illustrating the mitral valve from the left atrium after tissue plication with the first and second tissue anchors positioned at the P3 and A3 regions, respectively, and third and fourth tissue anchors positioned at the P1 and A1 regions, respectively.

One example, shown in FIG. 17D, illustrates the use of four tissue anchors 182, 186, 198, 202, and can be the combination of the embodiments shown in FIGS. 17B-C. The use of four tissue anchors 182, 186, 198, 202, spanning the mitral valve 56 at two regions, as shown, can provide improved reduction in the mitral valve size and further reduce mitral regurgitation. Also, as shown in FIG. 17D, the position of the lockers 194, 212 can be adjusted to the particular needs or preferences of the physician.

Figure 17E:
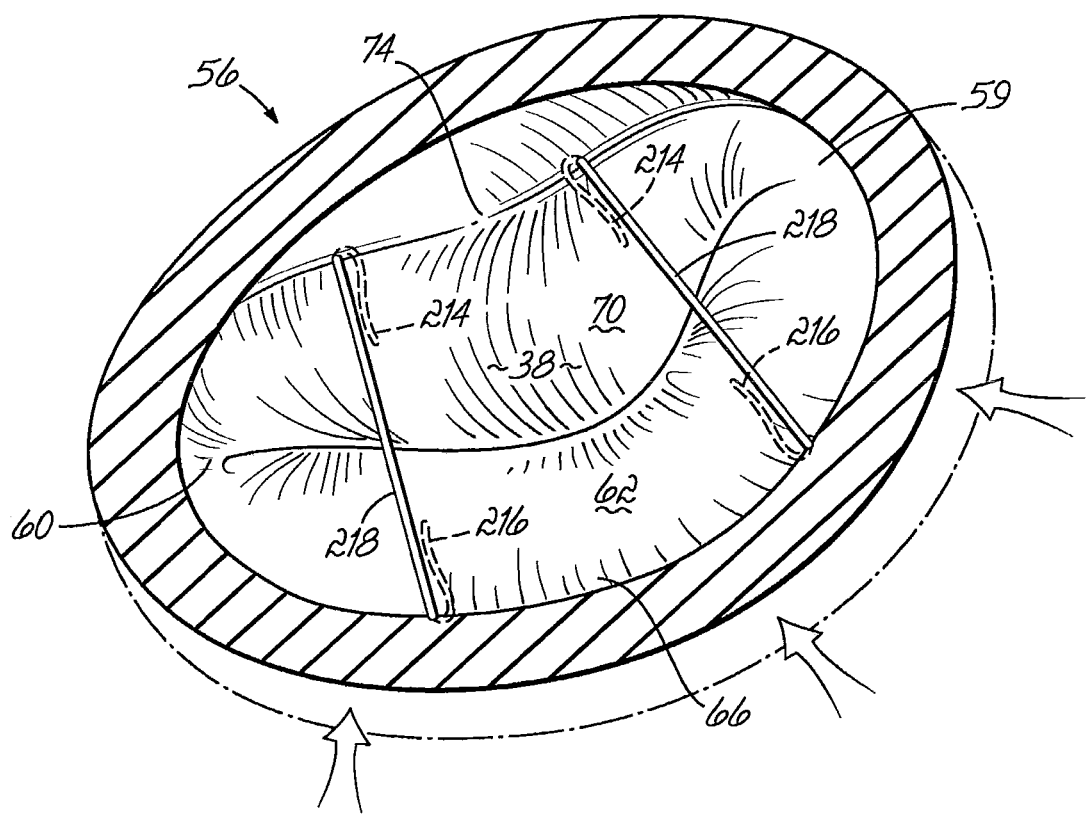
FIG. 17E is a top view illustrating the mitral valve from the left atrium after tissue plication and with a first staple positioned between the P3 and A3 regions and a second staple positioned between the P1 and A1 regions.

Alternatively, FIG. 17E illustrates the use of first and second legs 214, 216 and the base 218 of two staples as the tissue anchor and tensile members, respectively. The first and second staples can be positioned in a manner that is similar to the tissue anchors 182, 186, 198, 202 of FIG. 17D to pull the posterior annulus 66 toward the anterior or annulus 74 and effectuate mitral valve repair.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A method of repairing a mitral heart valve, the mitral heart valve having posterior and anterior leaflets forming an orifice therebetween, an annulus surrounding the posterior and anterior leaflets, and posterior and anterior commissures where the posterior and anterior leaflets join the annulus, the method comprising:
   (a) directing a first guide-wire into the right atrium, across an intra-atrial septum, into the left atrium, and to a first position of the annulus between the posterior and anterior commissures;
   (b) advancing a first tissue anchor along the first guide-wire to the first position of the annulus, wherein the first tissue anchor comprises a plurality of discrete flat flexible anchor elements;
   (c) securing the first tissue anchor to the first position of the annulus by partially deploying a portion of the first tissue anchor within the left ventricle such that a first plurality of discrete flat flexible anchor elements are disposed and in contact with one another on a first side of the annulus and then deploying a remainder of the first tissue anchor within the left atrium such that a second plurality of discrete flat flexible anchor elements are disposed and in contact with one another on a second side of the annulus;
   (d) directing a second guide-wire into the right atrium, across the intra-atrial septum, into the left atrium, and to a second position portion of the annulus between the posterior and anterior commissures;

(e) advancing a second tissue anchor along the second guide-wire to the second position of the annulus, wherein the second tissue anchor comprises a plurality of discrete flat flexible anchor elements;

(f) securing the second tissue anchor to the second position of the annulus by partially deploying a portion of the second tissue anchor within the left ventricle such that a first plurality of discrete flat flexible anchor elements are disposed and in contact with one another in stacked relationship on the first side of the annulus and then deploying a remainder of the second tissue anchor within the left atrium such that a second plurality of discrete flat flexible anchor elements are disposed and in contact with one another in stacked relationship on a second side of the annulus; and (g) spanning the first and second tensile members across the annulus and applying tension to the first and second tensile members, thereby pulling the first portion of the annulus toward the second portion of the annulus;

wherein the step (c) of securing the first tissue anchor includes the step of applying tension to a first tensile member and the step (f) of securing the second tissue anchor includes applying tension to a second tensile member, wherein the first and second tensile members are distinct and separate from one another.

2. The method according to claim 1, wherein the steps (a)-(g) are performed percutaneously with at least one catheter.

3. The method according to claim 2, wherein the at least one catheter is percutaneously directed into the right atrium through the inferior or superior vena cava.

4. The method according to claim 1 further comprising: maintaining the tension applied to the at least one tensile member with a suture locker.

5. The method according to claim 1, wherein the posterior leaflet includes P1, P2, and P3 regions and the anterior leaflet includes A1, A2, and A3 regions, the first position is located on a posterior portion of the annulus being at the P1 region and the second position is located on an anterior portion of the annulus being at the A1 region.

6. The method according to claim 1, wherein the posterior leaflet includes P1, P2, and P3 regions and the anterior leaflet includes A1, A2, and A3 regions, the first position is located on a posterior portion of the annulus being at the P3 region and the second position is located on an anterior portion of the annulus being at the A3 region.

7. The method according to claim 1, further comprising:

(h) directing a third guide-wire into the right atrium, across the intra-atrial septum, into the left atrium, and to a third position of the annulus between the posterior and anterior commissures;

(i) advancing a third tissue anchor to the third position of the annulus, wherein the third tissue anchor comprises a plurality of discrete flat flexible anchor elements;

(j) securing the third tissue anchor to the third position of the annulus;

(k) directing a fourth guide-wire into the right atrium, across the intra-atrial septum, into the left atrium, and to a fourth position of the annulus between the posterior and anterior commissures;

(l) advancing a fourth tissue anchor to the fourth position of the annulus, wherein the fourth tissue anchor comprises a plurality of discrete flat flexible anchor elements;

(m) securing the fourth tissue anchor to the fourth position of the annulus;

wherein the step (k) of securing the third tissue anchor includes the step of applying tension to a third tensile member and the step (n) of securing the fourth tissue anchor includes applying tension to a fourth tensile member.

8. The method according to claim 7, wherein the posterior leaflet includes P1, P2, and P3 regions and the anterior leaflet includes A1, A2, and A3 regions, the first position being located on a posterior portion of the annulus at the P1 region, the second position being located on the posterior portion of the annulus at the P3 region, the third position being located on an anterior portion of the annulus at the A1 region, and the fourth position being located on the anterior portion of the annulus being at the A3 region.

9. The method of claim 7, further including the steps of (n) spanning the third and fourth tensile members between the third and fourth tissue anchors and across the orifice of the mitral valve; and (o) applying tension to the third and fourth tensile members to further pull the first portion of the annulus toward the second portion of the annulus.

\* \* \* \* \*